United States Patent [19]

Kaplan et al.

[11] Patent Number: 5,250,031
[45] Date of Patent: Oct. 5, 1993

[54] LOCKING NEEDLE COVER

[75] Inventors: Lee D. Kaplan, Washington, D.C.;
Richard Hitzelberg, Catlett, Va.

[73] Assignee: The George Washington University, Washington, D.C.

[21] Appl. No.: 990,153

[22] Filed: Dec. 14, 1992

[51] Int. Cl.⁵ ............................................. A61M 5/00
[52] U.S. Cl. ............................. 604/110; 604/192; 604/198
[58] Field of Search ............ 604/110, 187, 192, 198, 604/263

[56] References Cited

U.S. PATENT DOCUMENTS

| | | | |
|---|---|---|---|
| 4,139,009 | 2/1979 | Alvarez | 604/198 |
| 4,725,267 | 2/1988 | Vaillancourt | 604/192 |
| 4,735,618 | 4/1988 | Hagen | 604/110 X |
| 4,867,172 | 9/1989 | Haber et al. | |
| 4,883,469 | 11/1989 | Glazier | 604/263 X |
| 4,892,521 | 1/1990 | Laico et al. | |
| 4,935,013 | 6/1990 | Haber et al. | |
| 4,950,250 | 8/1990 | Haber et al. | |
| 4,998,922 | 3/1991 | Kuracina et al. | 604/192 |
| 5,078,697 | 1/1992 | Rammler | |
| 5,114,409 | 5/1992 | Kole et al. | |

*Primary Examiner*—John D. Yasko
*Attorney, Agent, or Firm*—Quarles & Brady

[57] ABSTRACT

A locking protective cover for a needle or cannula of a hypodermic syringe, blood collector or other device includes a retractable cap member connected to the base of the needle by a resilient support that biases the cap member to a cover position around the needle tip. The cap member provides a needle channel for axial passage of the needle and a tip storage bore laterally connected to a needle channel through a one way locking path that permits transfer of the needle to the storage bore without removal of the tip from the cap member.

18 Claims, 3 Drawing Sheets

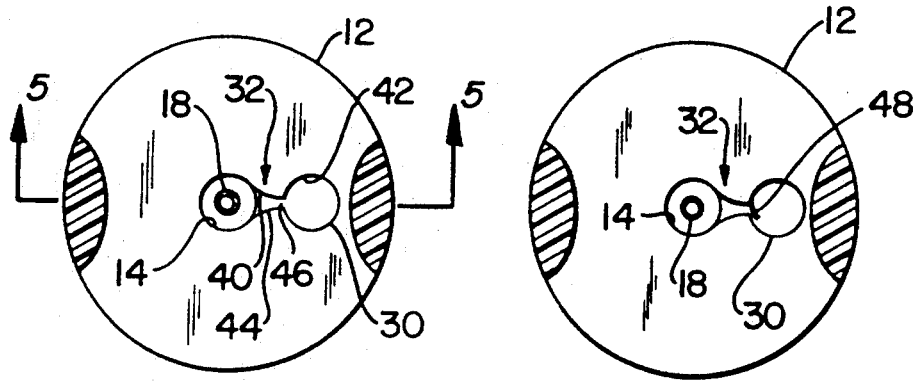
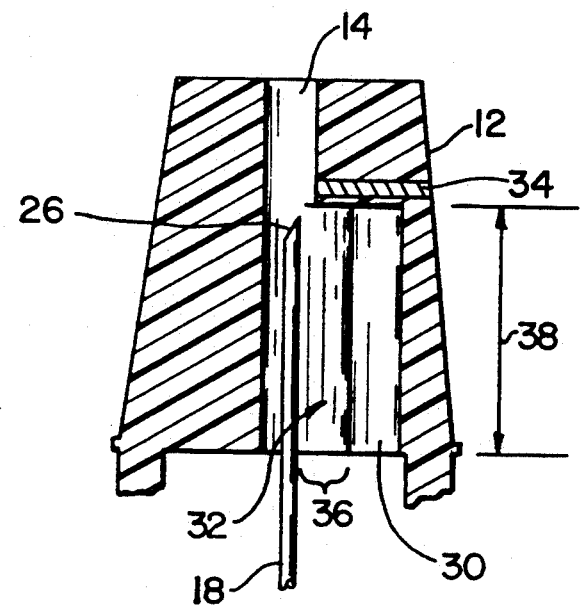

LOCKING NEEDLE COVER

FIELD OF THE INVENTION

The invention is directed to a cap for covering the tip of a needle of a syringe or other medical device. More particularly, the invention is concerned with a needle cap that is lockable in a tip covering position.

BACKGROUND OF THE INVENTION

Inadvertent punctures by used, potentially contaminated needles during disposal are a chronic problem in the medical industry. Such frequent accidents can subject the victim to hepatitis or even AIDS viral infection.

A variety of protective covers have been developed in the prior art in an effort to minimize the opportunity for puncture during the disposal of used needles. However, the closure methods required to lock the devices sometimes expose the user to the puncture danger which the covers are designed to eliminate.

SUMMARY OF THE INVENTION

Accordingly, it is an object of the invention to provide a needle cover to permanently cover the needle tip for safe disposal after use.

It is another object of the invention to provide a needle cover that can be manipulated to a locked position without exposing the user to inadvertent puncture.

It is yet another object of the invention to provide a locking needle cover which does not interfere with the normal operation of the needle during use.

It is still another object of the invention to provide a locking needle cover which is simple and economical to manufacture as a disposable unit with a disposable needle.

It is a further object of the invention to provide a needle cover that provides audible and visible indicia of positive locking.

These and other objects of the invention are met by a needle cover having a needle tip cap that continuously covers the needle tip except during actual use of the needle and can lockingly cover the tip without tip exposure during the locking process. The cap is preferably designed to be locked by a lateral manipulation of the device, away from the dangerous tip.

For normal operation of the needle, the cap member forms a channel through its length for passage of the needle. In a covering position, the cap surrounds the needle tip as it rests in 15 this cap channel. The cap can be suspended from the base of the needle by resilient support structure, such as spring arms, and can slidingly retract along the needle shaft by bending or contraction of the spring arms during insertion of the needle tip into a patient, vial or other surface. Upon withdrawal of the needle, the resilient support structure returns the needle cap to its original covering position, thereby placing the needle tip within the cap channel.

According to the invention, to permanently lock the tip within its confines, the cap provides internal locking means, such as a tip storage bore linked to the channel by a one way locking path. The bore is formed from the base side of the cap, substantially parallel to the channel, but does not extend through to the top of the cap as does the channel. Instead, the bore terminates at a depth roughly equal to the position of the tip end in the above described covered position.

The needle tip is transferred to the storage bore by laterally shifting through the locking path. This shift can be accomplished by relative movement of the cap member and the needle under side pressure to the support structure or the cap member. As the cover can be constructed in different sizes to accommodate different size needles, the manner of manipulation can vary.

The locking path is formed to readily allow passage of the needle tip to the storage bore but to impede return of the tip to the cap channel. The locking path can be constructed from a slightly deformable material, such as pliant plastic, and the path can taper to a width less than the width of the needle shaft at its juncture with the storage bore. Once the needle shaft passes the constriction into the bore, the resilient plastic path end returns to its narrow width, preventing return entry of the needle shaft. The snapping action of this return can also provide a clicking audible signal to indicate that positive locking has occurred.

The device can further be adapted to provide visual indication that locking has occurs. The spring arms can be equipped with lock rings to retain the spring arms in extended position after locking. Also, a latex sheath can enclose the device and rupture during use of the needle to signal use by its torn condition.

Thus, the needle tip can be permanently locked in the protective cap without even temporary withdrawal from the cap. The manipulation of the cover for locking can be performed by lateral pressure, transverse to and a distance away from the puncturing tip. This lateral action eliminates the need for axial hand motion toward the needle tip or attempted alignment of the needle tip with an intended storage place to lockingly cover the tip. Hence, the opportunity for inadvertent puncture during locking is substantially reduced relative to the attendant risks of prior devices.

BRIEF DESCRIPTION OF THE DRAWINGS

A greater understanding of the invention can be gained from reading of the following detailed description in conjunction with the drawings, in which:

FIG. 4a is a sectional view along line 4—4 in FIG. 2, showing a preferred locking structure in the cap member;

FIG. 4b is sectional view, similar to FIG. 4a, showing alternative locking structure utilizing a one-way flap;

FIG. 5 is a sectional view along line 5—5 in FIG. 4a; and

DETAILED DESCRIPTION OF THE PREFERRED EMBODIMENTS

The present invention is directed to a locking protective cover for the tip of a needle. The cover can be applied to needles or cannulas for syringes, blood collectors, vaccination bulbs, and any other apparatus in which the needles may be contaminated during use. The device can be constructed in varying sizes to accommodate the various needle sizes encountered. Throughout the following description, the exemplary embodiments are set forth in relation to a conventional hypodermic cannula for a syringe for illustration purposes only.

Figure 1:
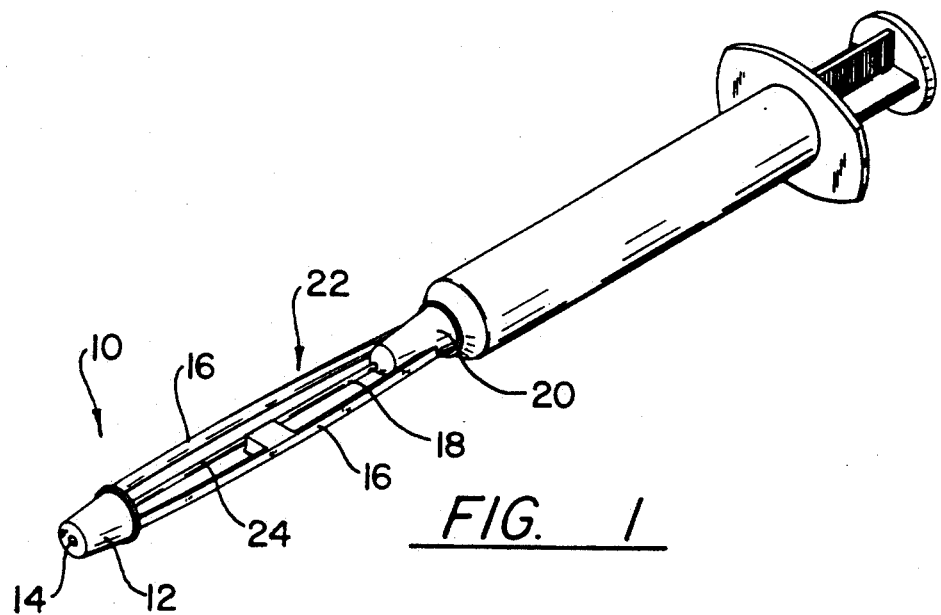
FIG. 1 is a perspective view of the cover of the invention as assembled on a hypodermic syringe.
Figure 3:
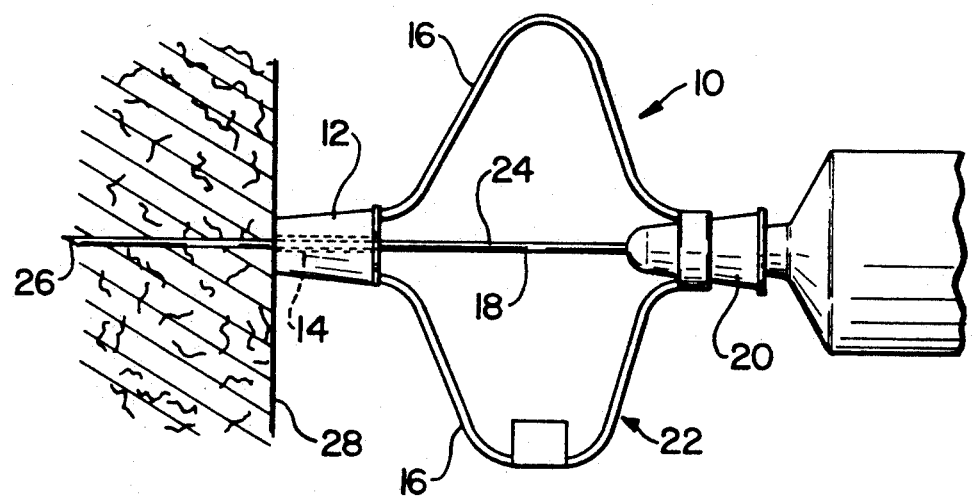
FIG. 3 is a side elevational view, similar to FIG. 2, showing the needle in an exposed position with the cap member retracted.

Referring to FIG. 1, the cover 10 includes means for covering, such as a cap member 12 having a needle channel 14 for passage of the needle 18 through the cap member 12. The cap member 12 extends from a base 20 of the needle by suspending means, such as a support 22 that is preferably, but not necessarily, resilient. The support 22 preferably has spring arms 16 that resiliently bias the cap member 12 over the tip of the needle 18 and permit retraction of the cap member 12 along the shaft 24 of the needle 18 to expose the needle tip 26 for use (FIG. 3).

Figure 2:
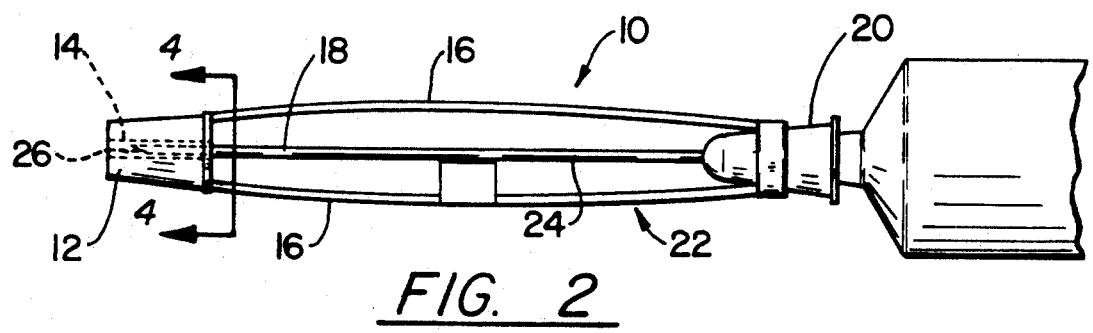
FIG. 2 is a side elevational view thereof, showing the needle in a covered position.

Referring to FIG. 2, the support 22 preferably biases the cap member 12 over the needle tip 26 in a cover position in which the tip 26 rests in the channel 14. During a puncture as shown in FIG. 3, the punctured substrate 28, such as a patient's skin or a vial cap, exerts pressure on the cap member 12 causing it to slidingly retract on the shaft 24 of the needle 18, against the resistance of the preferably resilient support 22, to expose the needle tip 26.

Referring to FIGS. 4 and 5, the cap member 12 includes internal locking means. The locking means preferably provides a tip storage bore 30 adjacent the channel 14 linked by a locking path 32. As best illustrated in FIG. 5, the storage bore 30 extends from the bottom of the cap member 12 substantially parallel to the channel 14 but terminates short of the top of the cap member 12. Preferably, the depth of the storage bore 30 is slightly greater than the depth of the needle tip 26 in the cover position and can be even greater. In the cover position, the needle 18 can be shifted to the storage bore 30 through the locking path 32 without removal from the cap member 12.

When the needle 18 is transferred to the storage bore 30, the tip 26 cannot be axially exposed because the terminus of the bore 30 prevents retraction of the cap member 12. The preferred plastic terminus formed by the cap member 12 can be reinforced such as by a small metal plate 34 to further prevent the needle tip 26 from passing through the plastic and being exposed.

The locking path 32 is preferably constructed to permit one way lateral passage of the needle 18 from the channel 14 to the storage bore 30 and thereafter to prevent return of the needle 18 to the channel 14. For orientation purposes, the locking path has a path length 36 in the direction from the channel 14 to the storage bore 30, a path height 38 parallel to the channel 14 and a path width 40 transverse to the path height 38 and path length 36.

To provide one way locking, the path width 40 preferably constricts along the path length 36 toward the storage bore 30. The entry to the locking path 32 at the channel 14 can be relatively wide and shallowly angled to readily receive the needle 18. At the junction between the path length end and the storage bore 30, the path width 40 preferably narrows to a width less than that of the needle 18.

To permit initial passage of the needle shaft 24 through the narrow constriction, the cap member 12, or at least that portion of the cap member 12 defining the locking path 32, can be formed of a deformable material, such a pliant plastic. Due to the gradual narrowing of the locking path 32 toward the storage bore 30 and the pressure applied to push the needle 18 through, the advancing needle 18 gradually expands the narrow width to freely pass; whereafter, the elastic material returns to its original position and presents a barrier to return. The snapping return can provide an audible clicking signal to confirm that a positive locking has occurred.

The storage bore surface 42 adjacent the locking path sidewalls 44 can also be formed to further impede return of the needle 18 to the channel 14. Unlike the shallowly sloping entry curves of the channel interface, the bore surface 42 can be formed substantially rectilinear to the path sidewalls 44, thereby forming an angle of 270 degrees. The surface 42 could even be angled further to provide curves away from the locking path opening 46.

The locking path 32 can also be formed with other one way locking constructions. For example, a flap 48 can be formed at the end of the locking path 32 into the storage bore 30. The flap 48 can be longer than the end width so that it bends into the storage bore 30 to allow entry of the needle 18 but is prevented from reverse bending by the surface of the storage bore 30.

The locking portion of the locking path 32 does not need to extend the entire height 38 of the locking path 32 but can alternatively be formed along only a portion of the height 38 to block a section of the needle shaft 24 away from the tip 26. Also, the constricted width can be provided over the entire length of the locking path 32 rather than tapered toward the storage bore 30.

Figure 6:
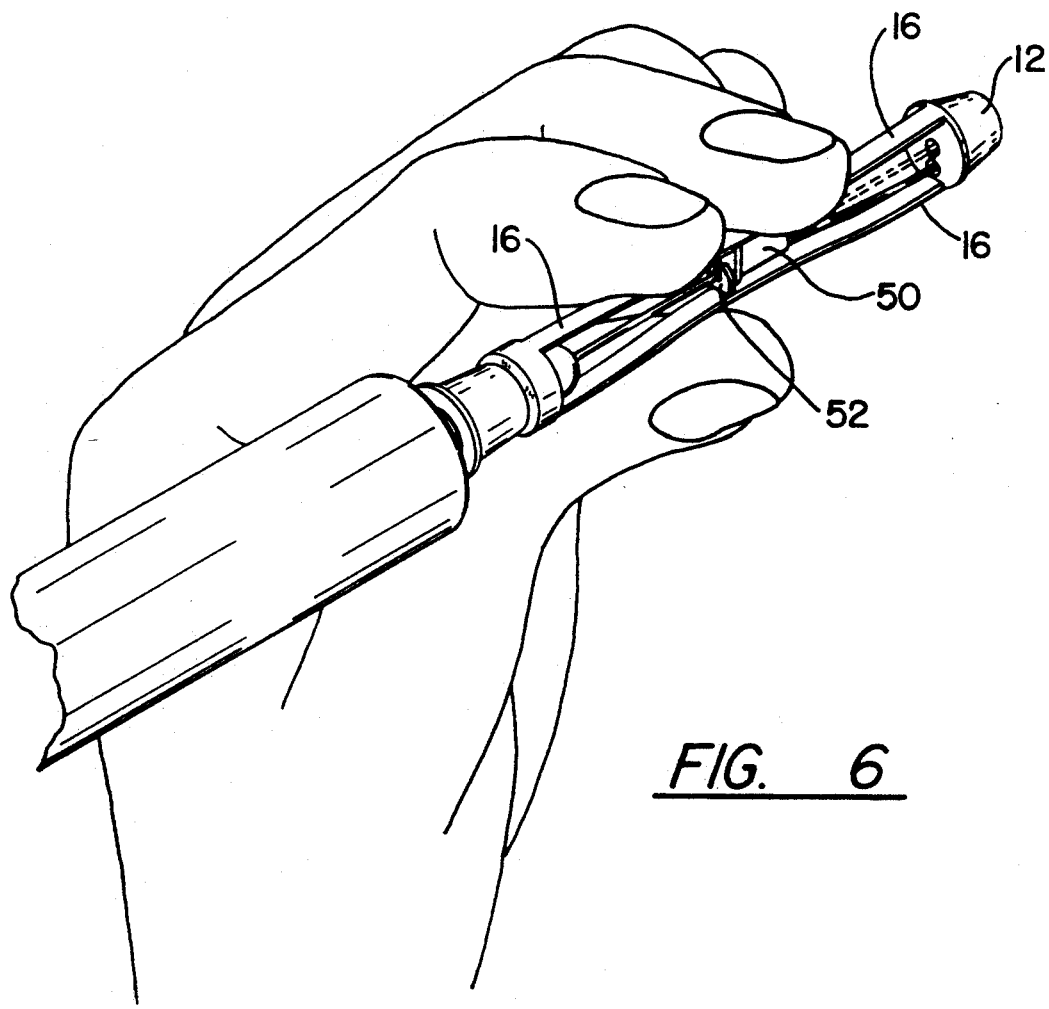
FIG. 6 is perspective view of an embodiment of the invention, illustrating a preferred technique for actuating the locking mechanism of the cover.

Referring to FIG. 6, after use, the needle tip 26 is automatically returned to the cove position within the channel 14 of the cap member 12 by the resilient spring arms 16. If the arms 16 are not resilient, the cap member 12 can be manually slid back to the cover position.

A pad 50 is preferably formed on one of the spring arms 16 for engagement with the needle shaft 24. The needle tip 26 can be transferred to the storage bore 30 by a variety of lateral manipulations depending on the size of the cover 10. For moderate sized systems, the spring arms 16 can be poised between the thumb on one spring arm and the fore and index fingers on the other spring arm. As the spring arms 16 are squeezed together, the pad 50 advances the needle 18 toward the storage bore 20 against the leverage provided by the opposite spring arm and fingers.

In larger and smaller versions of the cover, different grasping techniques may be used. Lateral pressure may be applied to the cap member or to varying parts of the spring arms. In all applications, it is possible to avoid axial hand or finger motion in the direction of the needle tip where slippage can lead to inadvertent puncture.

The spring arms 16 can optionally be equipped with C-clamps 52 which shackle the needle shaft 24 when the arms 16 are squeezed together and retain the spring arms 16 in the squeezed position. This secondary locking further prevents retraction of the cap member 12 and provides a visual signal that locking has occurred. The secondary locks can also be adapted to provide color indicia of locking, perhaps with red and green portions which are alternately covered depending on the position of the C-clamps 52.

Figure 7:
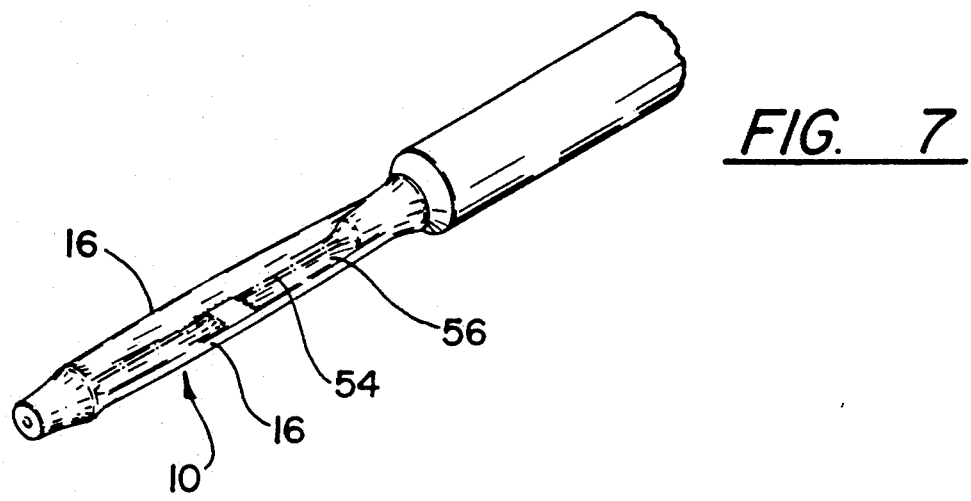
FIG. 7 is a perspective view of an alternative embodiment having a latex sheath.

Referring to FIG. 7, the cover 10 can be mounted on a disposable needle 54 as a preassembled unit to facilitate packaging and eventual use. The unit can be covered in a latex sheath 56. The latex sheath 56 can be provided in different colors to provide color coding for different sized needles or other variable parameters. The latex sheath 56 can also provide a vessel for enclosing blood and other fluids which may collect o the shaft of the needle 54 during use to prevent these fluids from dripping or otherwise spreading from the needle surface.

The latex can be thinly applied to permit transparent or translucent visibility of the interior components and can be so thin as to rupture when the spring arms 16 are retracted during use to provide a positive indicator to subsequent observers that the assembly has been used.

Although preferred features of the invention have been described with a relatively great degree of detail, it should be understood that many variations that still fall within the intended scope of the invention are possible. For example, the cap member is preferably round, but can be formed in other shapes and made of one material or a composite of materials. The support preferably includes a pair of bendable spring arms, but can have more arms. Alternatively, any resiliently bendable or compressible structure, such as a coiled shroud, can be utilized to support the cap member. The support can be integrally formed with the plastic base of a conventional, disposable cannula. Alternatively, the support can provide a base ring which threadably or otherwise securely mounts to a needle base to provide retrofit possibilities. To facilitate the cap member retraction, the preferred spring arms can be hinged by a reduction in material thickness at joints.

As many other variations will likely become apparent to those skilled in the art in view of the above teachings, the scope of the invention should not be determined by the foregoing discussion but rather from a reasonable interpretation of the appended claims.

We claim:

1. A cover for the tip of a needle for a medical device, the needle having a shaft extending down from the tip to a base, said cover comprising:
   means for covering the needle tip, said means for covering having an opening through which the needle tip and the needle shaft can axially extend to expose the needle tip from a top surface of the means for covering;
   means for suspending said means for covering and permitting said means for covering to retract toward the needle base to expose the needle tip for use and to extend to cover the needle tip after the use, said means for suspending being operatively connected between said means for covering and at least one of the needle base and the medical device;
   means for locking the needle tip in a storage position, said means for locking being disposed inside said means for covering and spaced from said top surface, said means for locking and said storage position being laterally offset from said opening, wherein the needle tip can transfer to the storage position laterally without withdrawal from the means for covering.

2. The cover according to claim 1, further comprising secondary locks mounted to the suspending means for latching to the needle shaft after use to prevent subsequent retraction of the covering means, said secondary locks providing a visual indication that locking has occurred.

3. The dispenser according to claim 1, wherein the cover is enclosed in a latex shroud.

4. A cover for the tip of a needle, the needle having a shaft extending down from the tip to a base, said cover comprising:
   a cap member having a channel extending from its bottom to its top for receipt and passage of the needle tip and shaft, said cap also forming a tip storage bore extending into said cap member from the bottom substantially parallel to said channel and terminating before the top, said storage bore and said channel being connected by a locking path, whereby when the needle tip is disposed in said channel, the tip can be slid laterally into said storage bore through said locking path without removal from said cap member; and
   a support connected to said cap member for suspending said cap member from the needle base, said support permitting said cap member to retract along the shaft to expose the needle tip from the cap member top and resiliently biasing said cap member to a cover position in which the needle tip is disposed inside said cap member.

5. The cover according to claim 4, wherein said locking path has a path length in the direction from said channel to said storage bore, a path height parallel to said channel and a path width transverse to said path height and said path length, said path width constricting along said path length toward said storage bore at least along a portion of said path height.

6. The cover according to claim 5, wherein an end width of said path width at the junction of said locking path and said storage bore is less than the width of the needle shaft.

7. The cover according to claim 6, wherein a portion of said cap member defining said locking path is made of a resiliently deformable material, whereby said end width can expand during transfer of the needle to the storage bore and return to its original width.

8. The cover according to claim 5, wherein the cap member surface defining said storage bore forms an angle of at least 270 degrees without an adjacent side wall of said locking path.

9. The cover according to claim 4, wherein a flap is formed in said cap member said flap blocking the locking path and being bendable in the direction of said storage bore.

10. The cover according to claim 4, wherein the support includes a plurality of spring arms connected between said cap member and the needle base, said spring arms being bendable to permit retraction of said cap member along the needle shaft and resiliently biasing said cap member to the cover position.

11. The cover according to claim 10, wherein said spring arms are hinged to facilitate bending.

12. The cover according to claim 10, wherein a pad is formed on one of said spring arms for engagement with the needle shaft, whereby the needle can be bent to transfer the needle tip to said storage bore by lateral pressure to the needle shaft through manipulation of said pad.

13. The cover according to claim 10, wherein said spring arms are integrally formed with the needle base.

14. The cover according to claim 19, wherein said spring arms are connected to a base ring that is mountable on the needle base.

15. The cover according to claim 14, wherein said base ring threads onto the needle base.

16. The cover according to claim 14, wherein said base ring slidingly mounts onto the needle base.

17. The cover according to claim 4, wherein said locking path has a path length in the direction from said channel to said storage bore, a path height parallel to said channel and a path width transverse to said path height and said path length, said path width being less than the width of the needle shaft.

18. A method of safely using and disposing of a medical needle, comprising the steps of:
 covering a tip of the needle with a cap having an opening to permit passage of the needle;
 engaging the cap against a substrate for injection;
 exerting pressure on the cap so that the needle advances through the opening to enter the substrate;
 removing the needle from the substrate;
 returning the cap to cover position surrounding the needle tip;
 locking the needle tip in the cap by moving the needle and the cap laterally relative to each other, whereby the needle tip is permanently disaligned with the opening and cannot be exposed.

* * * * *